United States Patent [19]

Mohiuddin et al.

[11] Patent Number: 5,163,943

[45] Date of Patent: Nov. 17, 1992

[54] CIRCUMCISION INSTRUMENT WITH STAPLE MEANS

[76] Inventors: Mohammed M. Mohiuddin; Mohammed T. Mohiuddin, both of 5511 Shookstown Rd., Frederick, Md. 21701

[21] Appl. No.: 850,304

[22] Filed: Mar. 12, 1992

[51] Int. Cl.$^5$ .............................................. A61B 19/00
[52] U.S. Cl. .................................... 606/118; 606/219; 606/220; 227/175; 227/176; 227/180; 227/902
[58] Field of Search .............. 227/175, 902, 176, 180; 606/1, 118, 117, 139, 157, 174, 219, 220

[56] References Cited

U.S. PATENT DOCUMENTS

| | | |
|---|---|---|
| Re. 20,201 | 12/1936 | Sivon et al. |
| 1,765,319 | 6/1930 | Williams |
| 2,353,647 | 7/1944 | Carmichael |
| 2,705,958 | 4/1955 | Aki |
| 3,040,746 | 6/1962 | Chester |
| 3,566,873 | 3/1971 | Melges .................. 606/118 |
| 3,744,495 | 7/1973 | Johnson ................. 606/219 |
| 3,789,848 | 2/1974 | Honjyo |
| 3,892,242 | 7/1975 | Honjyo .................. 606/118 |
| 4,111,206 | 9/1978 | Vishnevsky et al. ...... 227/176 |
| 4,491,136 | 1/1985 | Leveen |
| 4,520,817 | 6/1985 | Green ................... 227/176 |
| 4,602,634 | 7/1986 | Barkley ................. 227/180 |
| 4,648,401 | 3/1987 | Mattson |
| 4,788,978 | 12/1988 | Strekopytov et al. ..... 227/176 |
| 5,100,042 | 3/1992 | Gravener et al. ........ 227/176 |

FOREIGN PATENT DOCUMENTS

| | | | |
|---|---|---|---|
| 0324637 | 7/1989 | European Pat. Off. | 227/175 |
| 1391628 | 4/1988 | U.S.S.R. | 227/175 |
| 8101958 | 7/1981 | World Int. Prop. O. | 227/175 |

*Primary Examiner*—Stephen C. Pellegrino
*Assistant Examiner*—Glenn Dawson
*Attorney, Agent, or Firm*—Laubscher & Laubscher

[57] ABSTRACT

A circumcision instrument includes a pair of body members displaceable toward each other to simultaneously cut the foreskin along a longitudinal or circumferential line of cut while simultaneously stapling together the skin and mucous layers of the foreskin along at least one stapling line generally parallel with the cut, thereby to reduce bleeding from a cut. In a first embodiment, a generally straight cutting blade is carried by a body member at one end of a pair of scissors-type arms for longitudinally cutting the foreskin, cooperating male and female staple members being removably mounted on opposed body members for simultaneously producing stapling lines on both sides of the cut. In a second embodiment, a pair of annular body members arranged concentrically about a penis are displaced together on opposite sides of the foreskin when folded concentrically back around one of the annular members, a circular stapling line being defined concentrically between a circular cut and the penis. In a third embodiment, a cutting blade is arranged on a body member at one end of an arm of a scissors-type device for intermittently snipping and simultaneously stapling the foreskin along a line extending circumferentially of the penis.

26 Claims, 3 Drawing Sheets

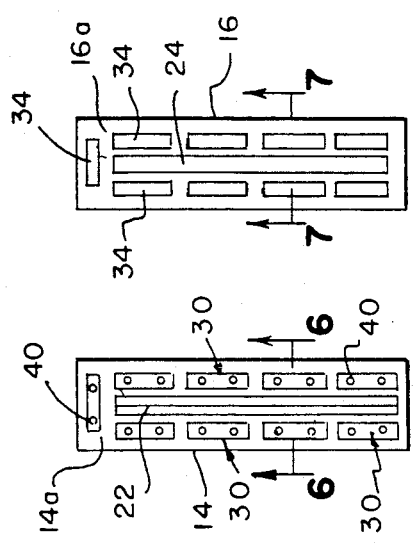
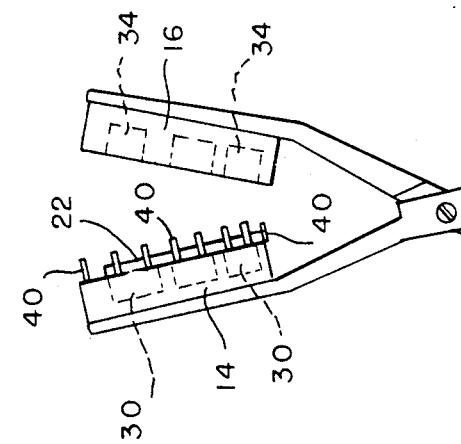
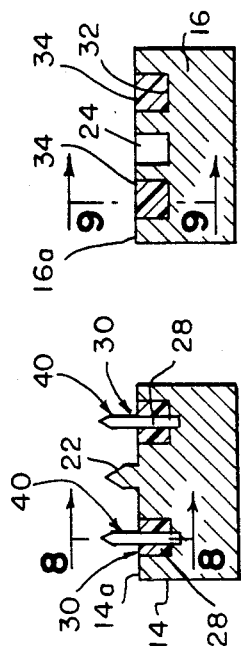
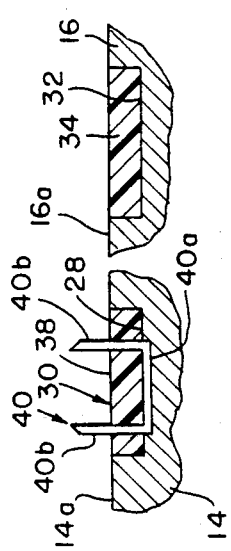
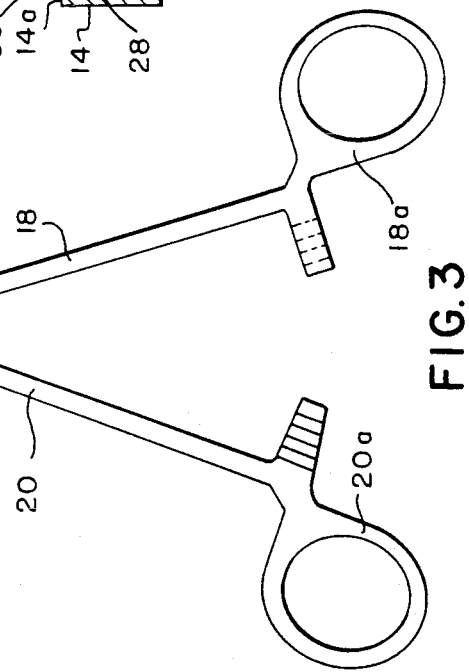
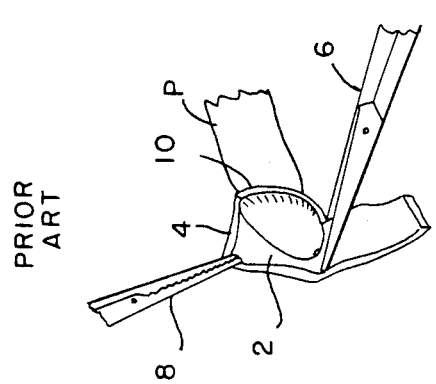
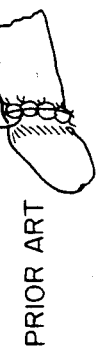

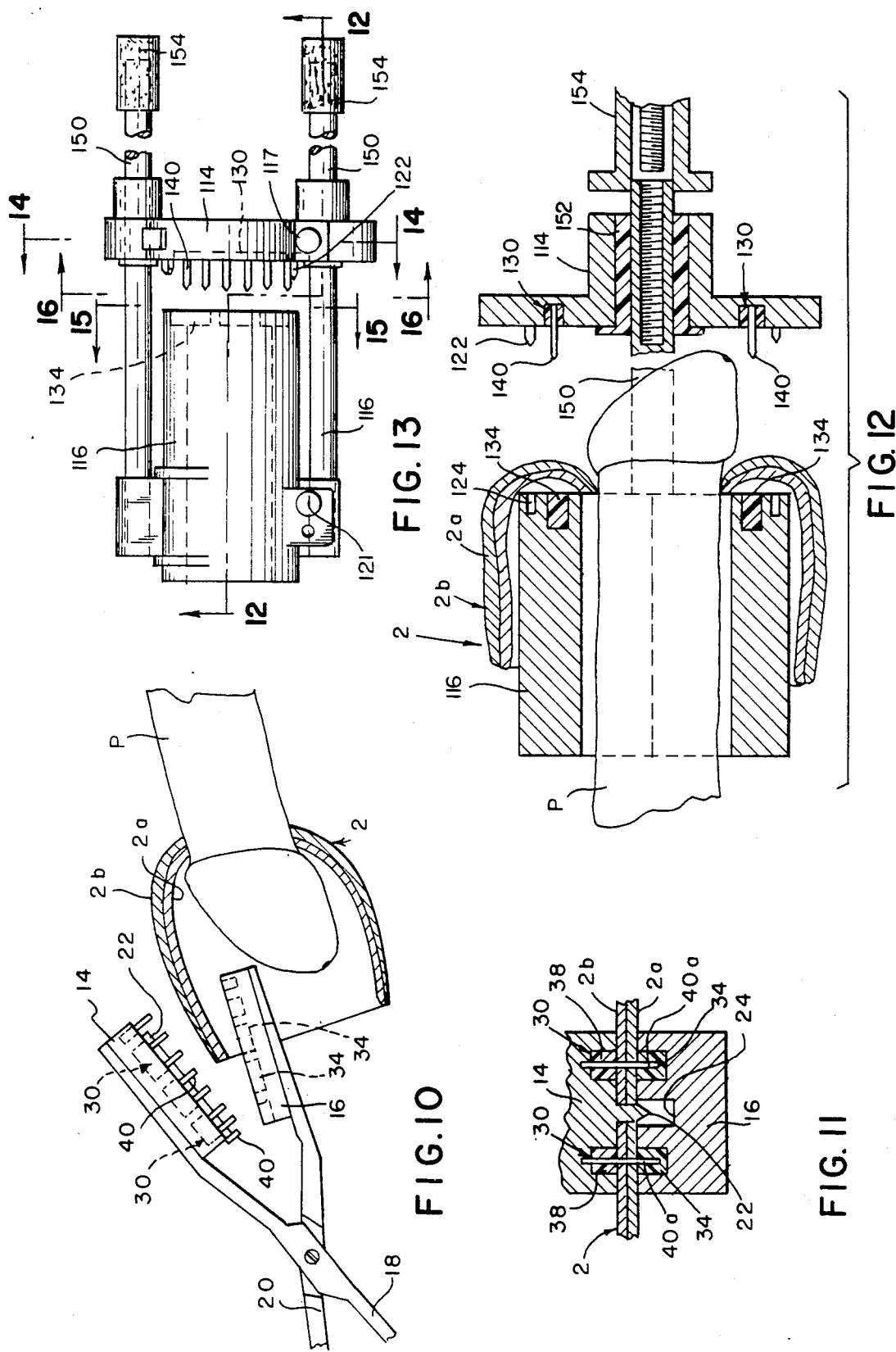

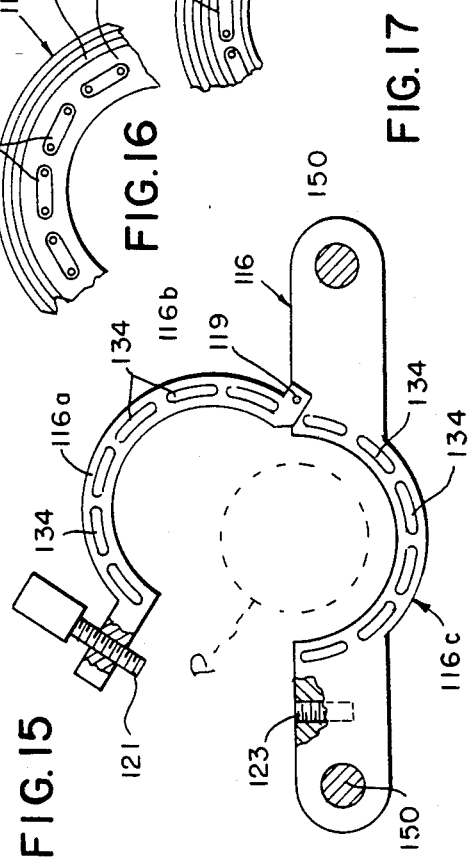

CIRCUMCISION INSTRUMENT WITH STAPLE MEANS

STATEMENT OF THE INVENTION

A circumcision instrument is provided including a pair of body members that are displaceable together on opposite sides of the foreskin of a penis to simultaneously cut the foreskin and to staple and clamp together the mucous and skin layers thereof along a stapling line adjacent and generally parallel with the line of cut, thereby to prevent bleeding from the cut.

BRIEF DESCRIPTION OF THE PRIOR ART

Circumcision instruments are well known in the medical surgery art, as evidenced, for example, by the prior patents to Carmichael No. 2,353,647 and Mattson No 4,648,401, among others. It is customary in surgical procedures to sever the foreskin from the penis, and then to manually stitch or suture the remaining portion of the foreskin to stop the bleeding from the severed blood vessels. Such a circumcision procedure normally takes about twenty to thirty minutes, and occasionally produces adverse effects, such as infection or the like.

The present invention was developed to provide an improved circumcision instrument which not only substantially reduces the time required for performing a circumcision operation, but also reduces bleeding and the attendant possibility of infection, results in a greatly shortened healing time, and avoids the use of stitches and, consequently, subsequent stitch removal.

SUMMARY OF THE INVENTION

Accordingly, a primary object of the invention is to provide an improved circumcision instrument including a pair of body members that are displaceable together on opposite sides of the foreskin for simultaneously cutting the foreskin and stapling and clamping together the mucous membrane and skin layers thereof along a stapling line generally parallel with the line of cut, thereby to reduce bleeding from the cut layers.

According to a more specific object of the invention, at least one cutting blade is mounted on the face of one of the body members, and cooperating opposed male and female staple members are removably mounted on the adjacent faces of the body members along lines generally parallel with the edge of the cutting blade. In a first embodiment, the cutting blade is generally linear, and the body members are mounted on the ends of a pair of clamping arms of a scissors-like device, the cutting blade extending generally longitudinally of the associated arm for longitudinally cutting the foreskin by at least one cut. The adjacent faces of the body members on opposite sides of the foreskin are provided with removably mounted male and female staple members for simultaneously clamping together the skin and mucous layers of the foreskin along two stapling lines that extend parallel with and on opposite sides of the cutting blade, whereby both sides of each longitudinal cut are stapled along parallel stapling lines thereby to reduce bleeding.

According to another feature of the invention, a second embodiment of the circumcision instrument is utilized for circumferentially severing the longitudinally cut foreskin from the penis. In one form of this embodiment, a pair of colinearly arranged annular body members are provided that are axially displaceable together to circumferentially sever and staple the foreskin layers along concentric lines of cut and stapling, respectively. In a second form of this embodiment, the body members may be mounted in parallel relation at an angle on the adjacent ends of the arms of a scissors-type clamping device, a straight or slightly curved knife blade being provided on the face of one of the body members, and male and female staple members being mounted on the adjacent faces of the body members, whereby the foreskin may be progressively cut or snipped and simultaneously stapled along a stapling line between the cut and the penis by successively operating the instrument in a snipping manner circumferentially about the penis.

According to a more specific object of the invention, in the embodiment including a pair of axially displaceable annular members, the outer diameter of one of the annular body members is such that after the foreskin has been longitudinally cut and the penis has been inserted within the central opening of said one body member, the cut foreskin may be rolled back outwardly to a position arranged concentrically about the outer circumferential surface of the one annular body member, whereupon the annular second body member is then displaced toward the first body member to sever the foreskin about the penis, cooperating parts of male and female staple members removably mounted on the opposed faces of the body members being simultaneously engaged to clamp together the mucous membrane and skin layers of the foreskin along a circular stapling line concentrically arranged between the line of cut and the circumference of the penis. The annular body members may be slidably guided for linear relative displacement toward or away from each other, or they may be mounted at the adjacent ends of a pair of scissors-type clamping arms.

According to a further object of the invention, the pair of annular body members are each divided to define a pair of longitudinal sections that are hingedly connected together for displacement between open conditions for laterally receiving the penis, and closed conditions for encircling the penis. When the longitudinally cut foreskin is rolled outwardly to a position concentrically about the outer circumference said one annular body member, the body members are brought together to cut the foreskin along a circular circumferential line of cut while simultaneously stapling and clamping together the mucous membrane and skin layers along a line of stapling concentrically within the circular line of cut, thereby to prevent bleeding.

Another object of the invention is to provide novel circumcision staple means for reducing bleeding during the circumcision of a penis, including male and female staple members for clamping together the mucous membrane and skin layers of the foreskin simultaneously with the cutting of the foreskin. Cartridge means may be provided for mounting a plurality of the staple members on the face of a body member, thereby to expedite the staple loading operation.

BRIEF DESCRIPTION OF THE DRAWINGS

Other objects and advantages of the invention will become apparent from a study of the following specification when viewed in the light of the accompanying drawing, in which:

FIGS. 1 and 2 are perspective views illustrating the conventional surgical technique for circumcising a penis;

FIG. 3 is an elevational view of a first embodiment of the improved circumcision tool of the present invention for longitudinally cutting the foreskin;

FIGS. 4 and 5 are top plan views of the male and female body members of FIG. 3, respectively;

FIGS. 6 and 7 are sectional views taken along lines 6—6 and 7—7 of FIGS. 4 and 5, respectively;

FIGS. 8 and 9 are sectional views taken along lines 8—8 and 9—9 of FIGS. 6 and 7, respectively;

FIG. 10 is a partly broken away diagrammatic view illustrating the manner in which the instrument of FIG. 3 may be used to longitudinally cut and staple the foreskin;

FIG. 11 is a detailed sectional view illustrating the simultaneous cutting and stapling of the foreskin by the instrument of FIG. 3;

FIG. 12 is a longitudinal sectional view taken along line 12—12 of FIG. 13, illustrating the manner of use of a second embodiment of the invention in circumferentially cutting the foreskin relative to the penis;

FIG. 13 is a top plan view of the instrument of FIG. 12 with the body sections thereof in the closed condition;

FIGS. 14—16 are sectional views taken along lines 14—14, 15—15 and 16—16, respectively, of FIG. 13, the body sections being pivoted to the open condition;

FIG. 17 is a detailed end view of a portion of the annular body member including cartridge means for supporting the staple members;

FIG. 18 illustrates another modification of the apparatus of FIGS. 12 and 13;

FIG. 19 is an illustration of a third embodiment of the invention;

FIGS. 20 and 21 are sectional views taken along lines 20—20 and 21—21 of FIG. 19, respectively; and FIGS. 22 and 23 illustrate the circumferential circumcision procedure using the instrument of FIG. 19.

DETAILED DESCRIPTION

Referring first more particularly to FIGS. 1 and 2, in performing a customary circumcision operation, the surgeon initially cuts the foreskin 2 along a first longitudinal line of cut 4, whereupon the foreskin is cut circumferentially by the cutting scissors 6 while held away from the head of the penis P by the tweezer means 8. As shown in FIG. 2, the line circumferential cut 10 is subsequently held together by a plurality of circumferentially spaced stitches 12. After the severed area has healed, the stitches are removed in a conventional manner. This known procedure often produces a substantial amount of bleeding from the foreskin, particularly when a vein or artery is severed during the circumcision surgery.

Referring now to FIG. 3, a first embodiment of the invention is disclosed including means for simultaneously cutting and stapling together the foreskin layers, thereby to reduce bleeding. More particularly, the instrument includes a pair of body members 14 and 16 mounted on the ends of a pair of scissors-type arms 18 and 20 that are pivotally connected intermediate their ends. In this embodiment, the body members extend longitudinally of the arms and are secured in opposed relation between the free ends thereof. The first body member 14 contains a longitudinally extending knife blade 22 having a straight cutting edge, and the adjacent face of the other body member 16 contains a corresponding longitudinal groove 24 for receiving the knife blade when the arms 18 and 20 are operated to displace together the body members 14 and 16, respectively. In accordance with a characterizing feature of the invention, the face 14a of body member 14 adjacent the other body member 16 contains a plurality of recesses 28 for receiving male staple members 30, respectively. As shown in FIG. 4, the male staple members 30 are arranged to define a pair of parallel straight lines of stapling on opposite sides of the cutting blade 22, and the opposed face 16a of the other body member 16 contains corresponding recesses 32 for receiving female staple blocks 34, respectively. As shown in FIGS. 6 and 8, each male staple member 30 includes a synthetic plastic support block 38 formed of a suitable synthetic plastic material, such as polyurethane, in combination with a metal staple member 40 formed of stainless steel or the like, which staple member includes a base portion 40a and a pair of arm portions 40b that terminate in pointed extremities. The coefficient of hardness of the female staple block 34 is such as to permit penetration by the pointed arm portion 40b of the staple 40, while simultaneously gripping the same when in a clamped condition, as will be described below with regard to FIG. 11. The body members 14 and 16 are preferably formed of metal, such as stainless steel, bronze, or the like, although it is possible that they might be formed from a suitable hard synthetic plastic material.

Referring now to FIGS. 10 and 11, in order to initially cut the foreskin 2 longitudinally, the instrument is positioned with the body members 14 and arranged on opposite sides of the foreskin, whereupon the finger portions 18a and 20b of the arms and 20 are brought together to pivot the arms together so that the pointed arm portions 40a of the staples are caused to pierce completely through the inner mucous membrane layer 2a and the outer skin layer 2b of the foreskin 2. As the body members 14 and 16 are further displaced together toward the clamping position of FIG. 11, the projecting pointed extremities of the arm portions 40a of the staples will partially pierce and extend within the female staple blocks 34, whereupon the staple blocks 38 and 34 are tightly compressed together on opposite sides of the skin and mucous membrane layers of the foreskin. Thus bleeding is reduced from the cut produced by the cutting edge of knife blade 22, which extends completely through the foreskin and terminates within the groove 24 contained in the face of the body member 16. The arms 18 and 20 are then pivoted apart to separate the body members 14 and 16, whereupon the male and female staple members remain in a clamped condition on opposite sides of the foreskin, thereby to prevent bleeding from the cut.

Referring now to FIGS. 12-16, a second embodiment of the invention is then utilized to circumferentially sever the longitudinally cut foreskin from the penis. More particularly, the circumcision instrument includes a pair of annular body members 114 and 116 that are arranged colinearly, the first body member 114 being guided for displacement toward and away from the second body member 116. More particularly, the second body member 116 includes a pair of parallel guide rails 150 upon which the first member 114 is slidably guided by means of annular synthetic plastic bushings 152, as shown in FIG. 14. Threadably connected with the free ends of the guide rods or rails 150 are a pair of clamping nuts 154. As shown in FIG. 14, the first body member is sectional and includes a cover portion 114b that is hingedly connected with the other section 114c by hinge means 115, a locking screw 117 being provided for locking the sections together following the insertion of a penis within the central openings of the body members. Similarly, the second body member 116 includes a pair of longitudinally split sections 116b and 116c connected by hinge means 119, a locking screw 121 being provided for locking the sections together following the insertion of the penis. Referring to FIG. 15, the face 116a of the second body member 116 contains a plurality of circularly arranged recesses for receiving the female staple members 134, respectively. Similarly, the adjacent face 114a of the first body member 114 contains a plurality of circularly arranged recesses for receiving the male staple members 130, which staple members are concentrically arranged within the circular cutting edge defined by knife blade 122.

In operation, the second body member 116 is opened to the FIG. 15 condition, and the penis is inserted within the central opening, whereupon the cover section 116b is pivoted to the closed position and is locked by the cooperation between locking screw 121 and the threaded bore 123. The first body section 114 is then slidably mounted on the guide rods 140, whereupon the cover section 114b is pivoted to the closed position and is locked by the cooperation between locking screw 117 and threaded bore 125 contained in section 114c. The clamping screws 154 are then threadably connected with the extremities of guide rods 150, whereupon the clamping nuts 154 are rotated to progressively displace the body member 114 toward the body member 116. The projecting pointed ends of the arms of the staples 140 are caused to completely penetrate through the foreskin mucous membrane and skin layers and to partially extend within the corresponding female staple blocks 134, so that the male and female members are tightly clamped on opposite sides of the foreskin during the circumferential cutting of the foreskin by the circular knife blade 122, thereby to prevent bleeding from the cut foreskin. Following removal of the severed foreskin, the clamping nuts 154 are rotated in the opposite direction, and the locking screws 117 and 121 are unlocked, whereupon the cover sections 114b and 116b are pivoted toward their open positions. The instrument is then removed from the penis, and the male and female staple members remained in a tightly clamped condition on the portion of the foreskin that remains connected with the penis.

After several days of healing, the male and female members are separated manually in a simple manner. Consequently, it is obvious that in accordance with an important advantage of the present invention, the necessity of bandaging of the circumcised penis is avoided. Since the circumcision is accomplished in a relative bloodless manner, the possibility of infection is greatly reduced. Furthermore, the complete circumcision surgery requires only about 5 minutes or so, as distinguished from the customary 20 to 30 minute surgical procedure.

It is possible, in accordance with another important feature of the invention, to mount the male and female members in cartridge members which in turn are removably supported on the adjacent faces of the body members. As shown in FIG. 17, the male staple members 130 are removably mounted in openings contained in a cartridge member 160 that is removably mounted in an annular recess contained in the face 114a' of the first body member 114'. A similar cartridge may be provided in the adjacent face of the second body member 116 for removably supporting the female staple members. These cartridge members afford the advantage that a large number of staple members may be quickly mounted at one time on the face of the associated body member.

Instead of slidably guiding the annular members relative to each other, it is possible, as shown in FIG. 18, to mount the annular members 214 and 216 on the ends of scissor-like arms 118,120 of the clamping instrument.

Referring now to the third embodiment of FIGS. 19-21, the first and second body members 314 and 316 may be angularly mounted in parallel relationship on the ends of the arms 318 and 320 of the scissor-like arms of the clamping means. Thus, the male staple members 330 are arranged with their pointed staple arms 340a extending toward the female staple members 334 contained in corresponding recesses in the adjacent face 316a of the second body member 316. In this embodiment, the knife blade 322 may be either straight or be slightly curved, thereby to permit the instrument to be used for circumferentially cutting and stapling the foreskin intermittently along a circular path extending circumferentially of the penis, in place of the annular tool means of FIGS. 12-16. In the event that the cutting blade 322 is slightly curved, the line of stapling defined by the staple members 330 and 334 would be also curved and parallel with the cutting edge of the knife means 322. During circumferential cutting of the foreskin as shown in FIG. 22, the longitudinal cut of the foreskin is clamped together by means of the first staple means 334, while the portion of the circumferentially severed foreskin that remains attached to the penis is clamped by the second staple means 337, whereby upon removal of the severed foreskin, a circumferential line of stapling is defined by the second staple members 337 as shown in FIG. 23. After the wound has healed, the male and female staple portions are manually separated and removed from the penis.

While in accordance with the provisions of the patent statutes, the preferred forms and embodiments of the invention have been illustrated and described, it will be apparent to those skilled in the art that various changes and modifications may be made without deviating from the inventive concepts set forth above.

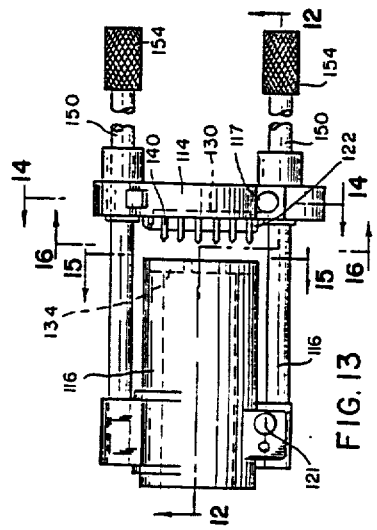
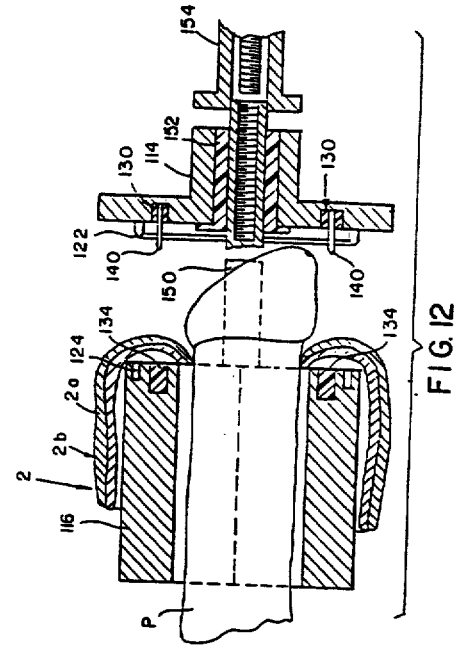

What is claimed is:

1. A circumcision instrument for use during the removal of the foreskin from the penis of a patient, said foreskin including an outer layer of skin, and a mucous membrane inner layer intermediate the skin layer and the penis, comprising:
   (a) first and second body members adapted for arrangement on opposite sides of the foreskin;
   (b) means for displacing said body members alternately toward and away from each other, respectively; and
   (c) means carried by said body members and operable when said body members are displaced together for simultaneously cutting the foreskin to define a line of cut and stapling together the mucous membrane and skinlayers of the foreskin adjacent said line of cut, thereby to reduce bleeding from the cut,
      (1) said cutting means including a knife blade mounted on said first body member adjacent said second body member;
      (2) said stapling means including a plurality of male staple members removably carried by at least one of said body members, said staple members including straight parallel pointed arms extending toward the other body member, and a plurality of cooperating female staple members at least some of which are carried by said other body member opposite said male staple members, respectively, said female members being generally inperforate and being formed of a synthetic plastic material having such a coefficient of hardness as to permit initial penetration thereof by the pointed extremities of said arms without bending of the arms, and subsequent retention of the unbent pointed arms to clamp together the male and female members on opposite sides of the foreskin.

2. Apparatus as defined in claim 1, wherein said knife blade has a straight cutting edge.

3. Apparatus as defined in claim 1, wherein said knife blade has a curved cutting edge.

4. Apparatus as defined in claim 1, wherein said body members are annular, colinearly arranged, and contain a central opening for receiving a penis to be circumcised, said knife blade being generally circular, whereby when the foreskin is longitudinally cut and rolled back concentrically about the outer circumferential surface of said second body member, displacement of said body members together causes the foreskin to be cut and stapled along concentric lines of cut and stapling, respectively, circumferentially of the penis.

5. Apparatus as defined in claim 4, wherein each of said body members includes a pair of hingedly connected longitudinally divided sections, the sections of one of said body members having end faces adjacent corresponding end faces of the sections of the other body member, respectively, and further wherein said knife blade includes a pair of generally semi-circular cutting edges arranged on the end faces of the sections of the first body member adjacent the corresponding section end faces of said second body member, said cutting edges defining a circular cutting line concentrically arranged about said central openings.

6. Apparatus as defined in claim 5, and further including means on each of said body members for fastening together the associated body sections.

7. Apparatus as defined in claim 5, wherein said staple means includes a plurality of said cooperating male and female staple members arranged on said adjacent end faces of said body member sections to define a circular stapling pattern concentrically within said cutting edges.

8. Apparatus as defined in claim 1, wherein said second body member contains a groove for receiving said knife blade.

9. Apparatus as defined in claim 1, wherein said scissors each of said male staple members includes a synthetic plastic support block, and at least one U-shaped metal staple having a transverse portion connected with said support block, and a pair of parallel arm portions that define said pointed arms.

10. Apparatus as defined in claim 9, wherein said body members include parallel adjacent faces containing opposed recesses for receiving cooperating male and female staple members, respectively.

11. Apparatus as defined in claim 9, wherein said body members include parallel adjacent faces containing opposed recesses, and further including cartridge members removably mounted in said recesses, said cartridge members containing recesses for removably receiving said male and female staple members, respectively.

12. Apparatus as defined in claim 1, wherein said body member displacing means comprises scissors means including a pair of scissors arms, said body members being mounted on corresponding first ends of said scissors arms, respectively, and finger-receiving portions at the other ends of said scissors arms, respectively, said arms being pivotally connected intermediate their ends.

13. Apparatus as defined in claim 12, wherein said members are arranged generally longitudinally of said scissors arms, respectively.

14. Apparatus as defined in claim 13, wherein said knife blade has a generally straight cutting edge extending generally longitudinally of the associated scissors arm for cutting the foreskin longitudinally.

15. Apparatus as defined in claim 14, wherein said stapling means defined lines of stapling on opposite sides of, and parallel with, the line of cut of said knife blade.

16. Apparatus as defined in claim 12, wherein said body members are generally parallel and are arranged at an angle relative to the associated scissors arms, respectively.

17. Apparatus as defined in claim 12, wherein said knife blade has a curved cutting edge, thereby to permit circumferential cutting and stapling of the foreskin adjacent the penis.

18. Apparatus as defined in claim 12 wherein said body members are annular, colinearly arranged, and contain aligned central openings for receiving the penis.

19. Apparatus as defined in claim 18, wherein said body member displacing means includes screw thread means.

20. Apparatus as defined in claim 19, and further including guide means guiding said body member for displacement toward and away from each other.

21. Apparatus as defined in claim 20, wherein said guide means includes a pair of parallel spaced guide rods upon which said second body member is slidably guided, and further wherein said screw thread means includes displacing nuts threadably connected with said guide rods, respectively.

22. Stapling means for reducing the bleeding from cut skin, such as a cut foreskin during the circumcision of a penis, which foreskin has a mucous membrane layer and a skin layer, comprising:

(a) a male staple member adapted for arrangement on one side of the foreskin, said male member including a synthetic plastic support block, and a generally U-shaped metal staple including a transverse portion connected with said support block, and a pair of parallel pointed arm portions that are adapted to extend toward the foreskin; and (b) a female staple member adapted for arrangement on the other side of the foreskin from said male member, said female staple member comprising a generally imperforate synthetic plastic block having a coefficient of hardness such as to permit penetration thereof by the pointed arm portion of said male staple members without bending thereof as said male and female staple members are displaced together to cause said staple arm portion to pierce the foreskin, said female plastic block being operable to retain said staple arm portion to clamp said blocks together on opposite sides of the foreskin, thereby to clamp together the mucous membrane and skin layers to prevent bleeding from the cut foreskin.

23. Apparatus as defined in claim 22, and further including a plurality of cartridge means supporting a plurality of said male and female staple members to define a given line of stapling, each of said cartridge means being adapted for mounting within a corresponding recess contained in the face of a circumcision instrument body member.

24. Apparatus as defined in claim 23, wherein said cartridge means includes a cartridge body containing a plurality of openings within which said staple members are removably supported, respectively.

25. Apparatus as defined in claim 22, and further including first and second body members carrying said male and female staple members opposite each other, respectively, and means for displacing said body members toward and away from each other, respectively.

26. Apparatus as defined in claim 25, and further including cutting means mounted on said first body member adjacent said second body member.

* * * * *

UNITED STATES PATENT AND TRADEMARK OFFICE
CERTIFICATE OF CORRECTION

PATENT NO. : 5,163,943　　　　　　　　　　　　　　　　　Page 1 of 3

DATED : November 17, 1992

INVENTOR(S) : Mohiuddin et al.

It is certified that error appears in the above-identified patent and that said Letters Patent is hereby corrected as shown below:

On the title page delete the drawings, and substitute therefor the drawings, consisting of Figs. 13 & 12, as shown on the attached page.

Signed and Sealed this

Eleventh Day of October, 1994

*Attest:*

BRUCE LEHMAN

*Attesting Officer*　　　*Commissioner of Patents and Trademarks*

United States Patent [19]
Mohiuddin et al.

[11] Patent Number: 5,163,943
[45] Date of Patent: Nov. 17, 1992

[54] CIRCUMCISION INSTRUMENT WITH STAPLE MEANS

[76] Inventors: Mohammed M. Mohiuddin; Mohammed T. Mohiuddin, both of 5511 Shookstown Rd., Frederick, Md. 21701

[21] Appl. No.: 850,304

[22] Filed: Mar. 12, 1992

[51] Int. Cl.⁵ .................................................. A61B 19/00
[52] U.S. Cl. .................................. 606/118; 606/219; 606/220; 227/175; 227/176; 227/180; 227/902
[58] Field of Search ............... 227/175, 902, 176, 180; 606/1, 118, 117, 139, 157, 174, 219, 220

[56] References Cited

U.S. PATENT DOCUMENTS

| | | | |
|---|---|---|---|
| Re. 20,201 | 12/1936 | Sivon et al. | |
| 1,765,319 | 6/1930 | Williams | |
| 2,353,647 | 7/1944 | Carmichael | |
| 2,705,958 | 4/1955 | Aki | |
| 3,040,746 | 6/1962 | Chester | |
| 3,566,873 | 3/1971 | Melges | 606/118 |
| 3,744,495 | 7/1973 | Johnson | 606/219 |
| 3,789,848 | 2/1974 | Honjyo | |
| 3,892,242 | 7/1975 | Honjyo | 606/118 |
| 4,111,206 | 9/1978 | Vishnevsky et al. | 227/176 |
| 4,491,136 | 1/1985 | Leveen | |
| 4,520,817 | 6/1985 | Green | 227/176 |
| 4,602,634 | 7/1986 | Barkley | 227/180 |
| 4,648,401 | 3/1987 | Mattson | |
| 4,788,978 | 12/1988 | Strekopytov et al. | 227/176 |
| 5,100,042 | 3/1992 | Gravener et al. | 227/176 |

FOREIGN PATENT DOCUMENTS

| | | | |
|---|---|---|---|
| 0324637 | 7/1989 | European Pat. Off. | 227/175 |
| 1391628 | 4/1988 | U.S.S.R. | 227/175 |
| 8101958 | 7/1981 | World Int. Prop. O. | 227/175 |

*Primary Examiner*—Stephen C. Pellegrino
*Assistant Examiner*—Glenn Dawson
*Attorney, Agent, or Firm*—Laubscher & Laubscher

[57] ABSTRACT

A circumcision instrument includes a pair of body members displaceable toward each other to simultaneously cut the foreskin along a longitudinal or circumferential line of cut while simultaneously stapling together the skin and mucous layers of the foreskin along at least one stapling line generally parallel with the cut, thereby to reduce bleeding from a cut. In a first embodiment, a generally straight cutting blade is carried by a body member at one end of a pair of scissors-type arms for longitudinally cutting the foreskin, cooperating male and female staple members being removably mounted on opposed body members for simultaneously producing stapling lines on both sides of the cut. In a second embodiment, a pair of annular body members arranged concentrically about a penis are displaced together on opposite sides of the foreskin when folded concentrically back around one of the annular members, a circular stapling line being defined concentrically between a circular cut and the penis. In a third embodiment, a cutting blade is arranged on a body member at one end of an arm of a scissors-type device for intermittently snipping and simultaneously stapling the foreskin along a line extending circumferentially of the penis.

26 Claims, 3 Drawing Sheets

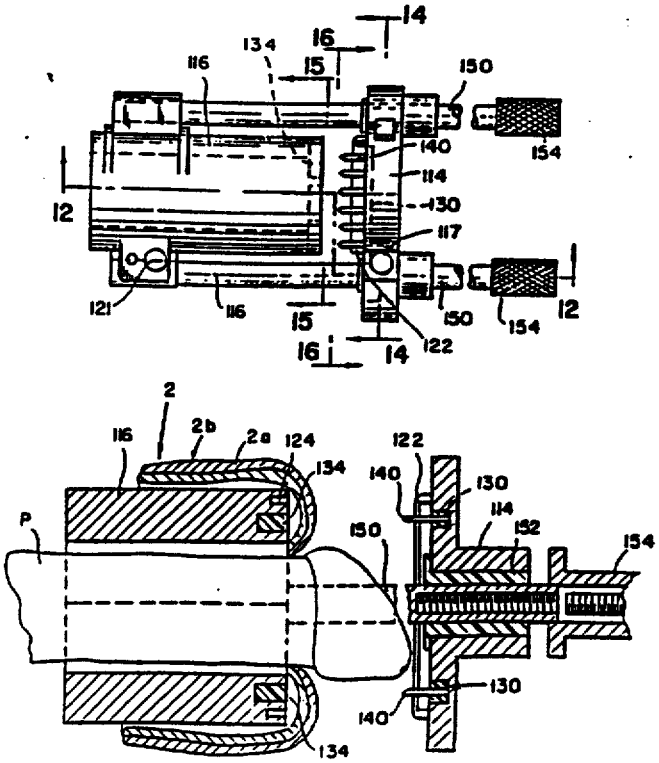

UNITED STATES PATENT AND TRADEMARK OFFICE
CERTIFICATE OF CORRECTION

PATENT NO. : 5,163,943                                Page 3 of 3
DATED      : November 17, 1992
INVENTOR(S): Mohiuddin et al It is certified that error appears in the above-identified patent and that said Letters Patent is hereby corrected as shown below:

In the drawings, sheet 2, figures 12 and 13 should appear as follows: